United States Patent [19]
Baker et al.

[11] Patent Number: 5,288,730
[45] Date of Patent: Feb. 22, 1994

[54] AZABICYCLIC COMPOUNDS, PHARMACEUTICAL COMPOSITIONS CONTAINING THEM AND THEIR USE IN THERAPY

[75] Inventors: Raymond Baker, Much Hadham; Christopher J. Swain, Duxford; Martin R. Teall, Standon; Brian J. Williams, Great Dunmow, all of England

[73] Assignee: Merck Sharp & Dohme Limited, Hoddesdon, England

[21] Appl. No.: 899,205

[22] Filed: Jun. 16, 1992

[30] Foreign Application Priority Data

Jun. 24, 1991 [GB] United Kingdom ............... 9113567

[51] Int. Cl.$^5$ ................... A61K 31/435; C07D 453/00
[52] U.S. Cl. ...................................... 514/305; 546/14; 546/137
[58] Field of Search ................. 546/14, 137; 514/305

[56] References Cited

U.S. PATENT DOCUMENTS

| | | | |
|---|---|---|---|
| 3,560,510 | 2/1971 | Warawa | 546/137 X |
| 3,833,592 | 9/1974 | Papanastassiou | 546/137 X |
| 4,599,344 | 7/1986 | Morgan, Jr. | 546/137 X |
| 4,843,074 | 6/1989 | Rzeszotarski et al. | 546/137 X |

FOREIGN PATENT DOCUMENTS

90/05729  5/1990  PCT Int'l Appl.

OTHER PUBLICATIONS

Otsuka, et al, "Role of Substance P As A Sensory Transmitter In Spinal Cord and Sympathetic Ganglia", 1982 Substance P in the Nervous System, CIBA Foundation Symposium 91, pp. 13-34.
Otsuka, TIPS, (Dec. 1987) vol. 8, pp. 506-510.
B. E. B. Sandberg, et al, J. Med. Chem. 1982, 25, No. 9 1009-1015.
Levine, et al Science, 1984 226, pp. 547-549.
Mantyh, et al, Neuroscience, 1988 25 (3) pp. 817-837.
D. Regoli, "Trends in Cluster Headache" Ed. Sicuteri, et al. Elsevier Scientific Publishers 1987 p. 85.
Kidd, et al, The Lancet, Nov. 11, 1989 "A Neurogenic Mechanism For Symmetrical Arthritis".
Grönblad, et al, "Neuropeptides In Synovium of Patients With Rheumatoid Arthritis & Osteoarthritis" J. Rheumatol 1988 15 (12) pp. 1807-1810.
O'Byrne, et al Arthritis & Rheumatism 1990, vol. 33, No. 7, pp. 1023-1028.
Kimball, et al, J. Immunol. 1988, 141 (10) pp. 3564-3569.
Mantyh, et al PNAS 1988, 85 pp. 3235-3239.
Yankner, et al Science, 1990 250 pp. 279-282.

Primary Examiner—Marianne M. Cintins
Assistant Examiner—Catherine S. Kilby Scalzo
Attorney, Agent, or Firm—Robert J. North; Charles M. Caruso

[57] ABSTRACT

Compounds of formula (I), and salts and prodrugs thereof:

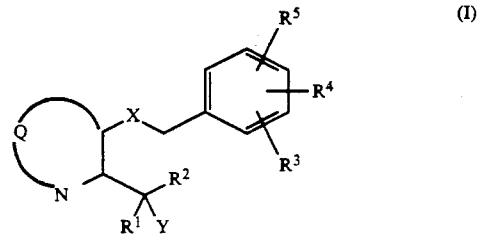

wherein
Q is the residue of an optionally substituted azabicyclic ring system;
X represents oxa or thia;
Y represents H or hydroxy;
$R^1$ represents phenyl or thienyl, either of which groups may be optionally substituted by halo, trifluoromethyl or $C_{1-3}$ alkoxy, or $C_{5-7}$ cycloalkyl;
$R^2$ represents benzyl which may be substituted in the benzyl ring by halo, trifluoromethyl or $C_{1-3}$ alkoxy, or $C_{5-7}$ cycloalkyl; and
$R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, —$OR^a$, $SCH_3$, $SOCH_3$, $SO_2CH_3$, —$NR^aR^b$, —$NR^aCOR^b$, —$NR^aCO_2R^b$, —$CO_2R^a$ or —$CONR^aR^b$; and
$R^a$ and $R^b$ independently represent H, $C_{1-6}$ alkyl, phenyl or trifluoromethyl, are tachykinin receptor antagonists. They and compositions thereof are useful in therapy.

11 Claims, No Drawings

AZABICYCLIC COMPOUNDS, PHARMACEUTICAL COMPOSITIONS CONTAINING THEM AND THEIR USE IN THERAPY

This invention relates to a class of azabicyclic compounds, which are useful as tachykinin antagonists. More particularly, the compounds of the invention comprise an azabicyclic ring system substituted by an arylmethyloxy or arylmethylthio moiety and by a benzyl- or cycloalkyl-methyl moiety, their preparation, formulations thereof and their use in medicine.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg-Pro-Lys-Pro-Gln-Gln-Phe-Phe-Gly-Leu-Met-NH₂

Neurokinin A:
His-Lys-Thr-Asp-Ser-Phe-Val-Gly-Leu-Met-NH₂

Neurokinin B:
Asp-Met-His-Asp-Phe-Phe-Val-Gly-Leu-Met-NH₂

For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (December 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, Nov. 11, 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9] vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al Science (1990) 250, 279–82] in senile dementia of the Alzheimer type, Alzheimer's disease and Downs Syndrome.

Substance P may also play a role in demyelinating diseases such as multiple sclerosis and amyotrophic lateral sclerosis [J. Luber-Narod et al, poster to be presented at C.I.N.P. XVIIIth Congress, Jun. 28–Jul. 2, 1992, in press].

In view of their metabolic instability, peptide derivatives are likely to be of limited utility as therapeutic agents. It is for this reason that non-peptide tachykinin antagonists are sought.

WO-A-90/05729 describes inter alia a class of cis-3-[cyclic]methylamino-2-[(α-substituted)-arylmethyl]-quinuclidine compounds which are stated to be useful as substance P antagonists for treating gastrointestinal disorders, central nervous system disorders, inflammatory diseases and pain or migraine. There is, however, no disclosure or suggestion in WO-A-90/05729 of the arylmethyloxy- or arylmethylthio-substituted azabicyclic derivatives provided by the present invention.

We have now found a further class of non-peptides which are potent antagonists of tachykinin.

The present invention provides a compound of formula (I), or a salt or prodrug thereof:

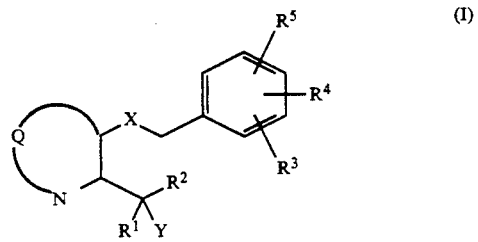

wherein

Q is the residue of an optionally substituted azabicyclic ring system;

X represents oxa or thia;

Y represents H or hydroxy;

R¹ represents phenyl or thienyl, either of which groups may be optionally substituted by halo, trifluoromethyl or C₁₋₃ alkoxy, or C₅₋₇ cycloalkyl;

R² represents benzyl which may be substituted in the benzyl ring by halo, trifluoromethyl or C₁₋₃ alkoxy, or C₅₋₇ cycloalkyl; and R³, R⁴ and R⁵ independently represent H, C₁₋₆ alkyl, C₂₋₆ alkenyl, C₂₋₆ alkynyl, halo, cyano, nitro, trifluoromethyl, trimethylsilyl, —ORᵃ, SCH₃, SOCH₃, SO₂CH₃, —NRᵃRᵇ, —NRᵃCORᵇ, —NRᵃCO₂Rᵇ, —CO₂Rᵃ or —CONRᵃRᵇ; and Rᵃ and Rᵇ independently represent H, C₁₋₆ alkyl, phenyl or trifluoromethyl.

The azabicyclic ring system of which Q is the residue is a non-aromatic ring system containing, as the sole heteroatom, the nitrogen atom indicated in formula (I) above. Suitably the ring system contains from 6 to 10 ring atoms, preferably from 7 to 9 ring atoms. The azabicyclic ring system may be fused, spiro or bridged, preferably bridged. The azabicyclic ring system may be substituted by one or more groups selected from carbonyl, C₁₋₄ alkyl, C₂₋₄ alkenyl, C₂₋₄ alkynyl, halo, hydroxy, C₁₋₄ alkoxy, carboxy or C₂₋₄ alkoxycarbonyl. Examples of such azabicyclic ring systems include:

(A)

-continued

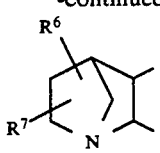
(B)

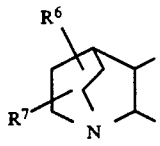
(C)

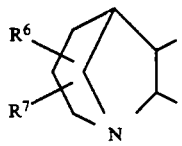
(D)

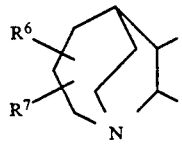
(E)

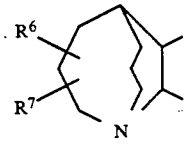
(F)

wherein $R^6$ and $R^7$ independently represent H, $C_{1-4}$ alkyl, $C_{2-4}$ alkenyl, $C_{2-4}$ alkynyl, halo, hydroxy, $C_{1-4}$ alkoxy, carboxy or ($C_{1-4}$ alkoxy)carbonyl; or $R^6$ and $R^7$ together represent carbonyl.

It will be appreciated that, except in the case of a quaternary ammonium salt, the nitrogen atom in the azabicyclic ring system will carry a lone pair of electrons.

It will also be appreciated that the $R^6$ and $R^7$ substituents may be present at any position in the azabicyclic ring system, including, where appropriate, the bridgehead carbon atom depicted in structures A to F above.

Suitably the group $R^6$ is H or methyl; and $R^7$ is H, $C_{1-4}$ alkyl, hydroxy or $C_{1-4}$ alkoxy, preferably H, methyl, hydroxy or methoxy. Preferably one or both of $R^6$ and $R^7$ is/are H.

Suitably the azabicyclic ring system of which Q is the residue of a 1-azabicyclo[2.2.1]heptanyl (1-azanorbornanyl), 1-azabicyclo[2.2.2]octanyl (quinuclidinyl) or 1-azabicyclo[3.2.1]octanyl ring system of formula (B), (C) or (D) above respectively, any of which is optionally substituted by methyl or hydroxy. A preferred ring system is quinuclidine of formula (C) above.

The alkyl, alkenyl and alkynyl groups referred to with respect to any of the formulae herein may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl and allyl; and suitable alkynyl groups include propargyl.

The term "halo" as used herein includes fluoro, chloro, bromo and iodo.

Preferably X is oxa.
Preferably Y is H.
Preferably $R^1$ represents unsubstituted phenyl or $C_{5-7}$ cycloalkyl such as cyclohexyl.

$R^1$ may also suitably be phenyl substituted by methoxy.

$R^2$ is preferably benzyl or cyclohexyl, more preferably benzyl.

Suitable values for the groups $R^3$, $R^4$ and $R^5$ include H, straight or branched $C_{1-6}$ alkyl, nitro, trifluoromethyl and halo, especially chloro. Preferably, at least one of $R^3$, $R^4$ and $R^5$ is other than H. Preferably, at least one of these is methyl or trifluromethyl. More preferably, $R^5$ is H, and $R^3$ and $R^4$ are present at the meta-positions of the aromatic ring. Especially preferred is when $R^3$ and $R^4$ are identical.

A particularly preferred subgroup of compounds of formula (I) are compounds wherein $R^3$ and $R^4$ are identical and are methyl or trifluoromethyl, more preferably trifluoromethyl.

The compounds according to the invention have at least two asymmetric centres, and may accordingly exist both as enantiomers and as diastereoisomers. In particular, the relative orientation of the 2- and 3-substituents on the azabicyclic ring system in formula (I) above may give rise to cis and trans diastereoisomers. It is to be understood that all such isomers and mixtures thereof are encompassed within the scope of the present invention.

It is believed that of the cis diastereomers, tachykinin receptor antagonist activity preferentially resides in the 2S,3S diastereomer, whereas of the trans diastereomers, activity preferentially resides in the 2R,3S diastereomers. Thus, it is believed that S stereochemistry at the 3-position of the azabicyle is crucial to tachykinin receptor antagonist activity.

A particular sub-class of compounds according to the invention is represented by the compounds of formula (IIA), and salts and prodrugs thereof:

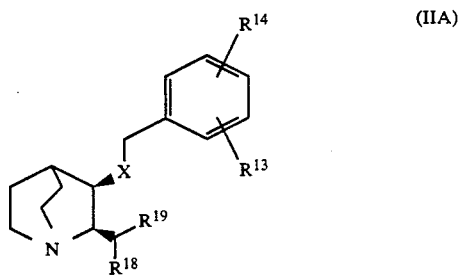
(IIA)

wherein
X represents oxa or thia, preferably oxa;
$R^{13}$ and $R^{14}$ independently represent hydrogen, $C_{1-6}$ alkyl, halo, cyano, nitro, trifluoromethyl, hydroxy, $C_{1-6}$ alkoxy or amino; and
$R^{18}$ is phenyl optionally substituted by halo, —$CF_3$ or $C_{1-3}$ alkoxy, or $C_{5-7}$ cycloalkyl; and
$R^{19}$ is benzyl or $C_{5-7}$ cycloalkyl.

Particular values of $R^{13}$ and $R^{14}$ include hydrogen, $C_{1-5}$ alkyl, especially methyl, halo, especially chloro and fluoro, nitro, trifluoromethyl, cyano, methyl and methoxy. Preferably, at least one of $R^{13}$ and $R^{14}$ is other than hydrogen.

A further sub-class of compounds according to the invention is represented by the compounds of formula (IIB), and salts and prodrugs thereof:

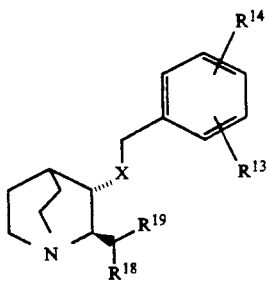

(IIB)

wherein X, $R^{13}$, $R^{14}$, $R^{18}$ and $R^{19}$ are as defined for formula (IIA) above.

A preferred group of compounds according to the invention are compounds of formula (IIB) wherein X is oxa and each of $R^{13}$ and $R^{14}$ represents a methyl or a trifluoromethyl group.

A further preferred group of compounds according to the invention are compounds of formula (IIB) wherein $R^{18}$ is substituted or unsubstituted phenyl and $R^{19}$ is benzyl.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, oxalic acid, fumaric acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The compounds of the present invention are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as MS and ALS and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. Thus, the present invention further provides a compound for use in the manufacture of a medicament for the treatment of physiological disorders associated with an excess of tachykinins, especially substance P. The present invention also provides a method for the the treatment or prevention of physiological disorders associated with an excess of tachykinins, especially substance P, which method comprises administration to a patient in need thereof of a tachykinin reducing amount of a compound or composition of this invention.

In the treatment of conditions involving actions of tachykinins released physiologically in response to noxious or other stimuli, a suitable dosage level is about 0.01 to 500 mg/kg per day, such as 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises reacting a compound of formula (III) with a compound of formula (IV):

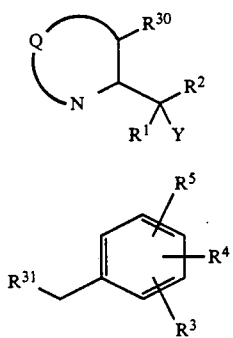

(III)

(IV)

wherein Q, Y, $R^1$, $R^2$, $R^3$, $R^4$ and $R^5$ are as defined for formula (I) above, and one of $R^{30}$ and $R^{31}$ represents a leaving group and the other of $R^{30}$ and $R^{31}$ represents XH, where X is as defined for formula (I); in the presence of a base.

Suitably, when Y is H, $R^{31}$ represents a leaving group and $R^{30}$ represents XH.

Suitable leaving groups include halo, e.g. chloro, bromo or iodo, or sulphonate derivatives such as tosylate or mesylate.

The reaction is conveniently carried out in a suitable organic solvent, such as an ether, e.g. 1,2-dimethoxyethane, at a temperature in the range of −5° to 25° C., preferably about 0° C. Favoured bases of use in the reaction include alkali metal amides and hydrides, such as potassium bis(trimethylsilyl)amide and potassium hydride. Suitably, potassium bis(trimethylsilyl)amide is used.

The intermediates of formula (III) above wherein $R^{30}$ is SH may be prepared from the corresponding intermediates of formula (III) wherein $R^{30}$ represents OH by treating the latter compound with Lawesson's reagent or phosphorus pentasulphide in a suitable solvent, e.g. pyridine, at ambient or elevated temperatures, suitably at reflux temperature.

The intermediates of formula (III) above wherein $R^{30}$ is OH and Y is H may be prepared by reduction of the corresponding ketone of formula (V)

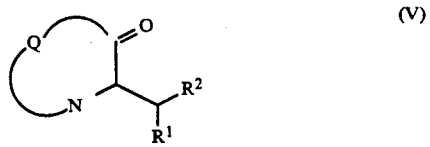

wherein $R^1$, $R^2$ and Q are as defined above. Suitable reducing agents will be readily apparent to a person skilled in the art and include, for example, metal hydrides, such as lithium aluminum hydride and sodium borohydride, or hydrogen in the presence of a catalyst, such as noble metal catalyst, e.g. palladium on charcoal. The reaction is conveniently effected in a suitable solvent. Suitable solvents will depend on the nature of the reducing agent employed and will be readily apparent to those skilled in the art.

The intermediates of formula (III) above wherein $R^{30}$ is OH and Y is hydroxy may be prepared by treatment of a compound of formula (VI) with a compound of formula (VII):

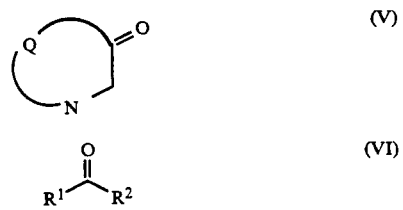

wherein Q, $R^1$ and $R^2$ are as defined for formula (I) above, in the presence of a base.

The reaction is conveniently carried out in an inert organic solvent, such as an ether, e.g. tetrahydrofuran, at low temperature, for example about −80° to about −40° C., preferably about −78° C. Suitable bases will be readily identified by a person skilled in the art and include alkali metal hydrides and amides. A favoured base is lithium bis(trimethylsilyl)amide.

Intermediates of formula (III) wherein $R^{30}$ is OH having cis stereochemistry may preferably be prepared from the corresponding ketones via a selective reduction using a suitable reducing agent such as a lithium aluminum hydride or a substituted borohydride such as triethylborohydride.

Intermediates of formula (III) wherein $R^{30}$ is OH having trans sterochemistry may be obtained selectively via a procedure involving non-selective reduction of the corresponding ketone, for example using sodium in an aromatic hydrocarbon solvent, e.g. toluene, preferably in the presence of an alcohol, e.g. iso-propyl alcohol, to give a mixture of cis and trans isomers, followed by selective oxidation of the cis isomer using a ketone in the presence of a base (Oppenauer oxidation). Suitable ketones include acetone, methyl ethyl ketone, cyclohexanone and, preferably, benzophenone. Suitable bases include alkali metal hydrides, e.g. potassium hydride.

Intermediates of formula (III) wherein $R^{30}$ is a leaving group may be prepared from compounds of formula (III) wherein $R^{30}$ is OH, for example, by reaction with a thionyl halide, a mesyl halide or a tosyl halide.

Ketones of formula (V) may be prepared from intermediates of formula (VIII)

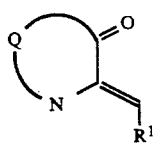
(VIII)

wherein R¹ and Q are as defined above, by reaction with a compound of formula R²MgHal, where Hal represents halo such as chloro, bromo or iodo.

Intermediates of formula (VIII) may be prepared by the procedures described in *J. Org. Chem.*, 1974, 39, 3511; or by methods analogous thereto.

Where they are not commercially available, the intermediates of formula (IV), (VI) and (VII) above may be prepared by conventional procedures which will be readily apparent to one skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, intermediate alcohols of formula (III), wherein X is oxa, may be resolved into their component enantiomers by standard techniques, such as the formation of diastereomeric esters or amides, followed by chromatographic separation and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

3-[(3,5-Dimethylphenyl)methyloxy]-2-(1,2-diphenylethyl)-1-azabicyclo[2.2.2]octane a)

2-(1,2-Diphenylethyl)-3-oxo-1azabicyclo[2.2.2]octane

To a stirred solution of 2-benzylidene-3-oxo-1-azabicyclo[2.2.2]octane (10 g) in diethyl ether (200 ml) at −10° C. under a nitrogen atmosphere was added a solution of 2M-benzylmagnesium chloride (30 ml, in tetrahydrofuran, 50 mmol) and diethyl ether (100 ml). The solution was stirred at −10° C. for 30 minutes and at ambient temperature for 16 h. A saturated solution of aqueous ammonium chloride (200 ml) was carefully added and the product extracted into ethyl acetate. The organic phase was dried (MgSO₄) and evaporated to dryness. The residue was chromatographed on a column containing silica gel 60 (220–440 mesh ASTM) eluting with mixtures of 30%, 50% and 70% ethyl acetate in petroleum ether (bp 60°–80° C.). 2-(1,2-diphenylethyl)-3-oxo1- azabicyclo [2.2.2]octane was obtained as 1:1 mixture of stereoisomers by evaporating the appropriate fractions.

b)

2-(1,2-Diphenylethyl)-3-hydroxy-1-azabicyclo[2.2.2]octane

To a solution of the product of Example 1a, (3.1 g; 1:1 mixture of diastereomers) in tetrahydrofuran (50 ml) at −78° C. was added a solution of 1M-lithium aluminum hydride (10.16 ml, in diethyl ether). After the solution had stirred at −78° C. for 2 h, water (3 ml) was added followed by aqueous 2M-sodium hydroxide (3 ml) and water (6 ml). When at room temperature, diethyl ether was added and the mixture filtered through Hyflo supercel. The ethereal phase of the filtrate was washed with water (2×30 ml), brine (30 ml) and dried (MgSO₄). After removal of the solvent in vacuo the residue was chromatographed on silica gel eluting with ethyl acetate/petroleum ether (bp 60°–80° C. (1:1)followed by methanol/ethyl acetate (1:50) to give the title compound as a mixture of stereoisomers.

c) 3-[(3,5-Dimethylphenyl)methyloxy[-2-(1,2-diphenylethyl)-1-azabicyclo[2.2.-2]octane hydrogen oxalate salt To a solution of alcohol (Example 1, 0.78 g, 1:1 mixture of stereoisomers) was added 0.5M-potassium hexamethyldisilazide (5.84 ml, in toluene). After 1 h, 3,5-dimethylbenzyl bromide (0.58 g) was added for 3 h. The solution was evaporated to dryness after a further 3 h, and the residue partitioned between dichloromethan and water. The organic phase was dried (MgSO₄), evaporated and purified by column chromatography on silica gel eluting with petroleum ether (bp 6014 80) containing increasing amounts of ethyl acetate (50% to 100%) and then methanol/ethyl acetate (15:85) to give a single diastereomer of the title compound. This was crystallised by addition of oxalic acid (72 mg) in propan-2-ol and diethyl ether to give 3-[(3,5-dimethylphenyl)methyloxy]-2-(1,2-diphenylethyl)-1-azabicyclo[2.2.2]octane hydrogen oxalate salt isomer A mp 64°–66° C.¹HNMR(DMSO,360MHz)δ 7.2–6.6 (13H,m,aryl), 4.6 (1H, d, J=16.0 Hz, OC$\underline{H}_A$H$_B$),4.4 (1H, d, J=16.0 Hz, OCH$_A\underline{H}_B$),3.5 (1H, m, OC$\overline{H}$CH),3.3 (1H, m, NC$\underline{H}_A$H$_B$), 2.99 $\overline{(1H}$, dd, NCHCH)),2.8–2.60 (5H, m, NCH$_A\underline{H}_B$,$\overline{N}$CH₂,PhC$\underline{H}_2$), 2.4(1H,m,PhC$\underline{H}$CH₂),2.3 (6H, s, CH₃, CH₃),2.25 $\overline{(1H}$, m, bridgehead $\overline{CH}$),1.9 (1H, m, $\overline{N}$CH₂C$\underline{H}_A$H$_B$),1.65 (1H, m, NCH₂CH$_A\underline{H}_B$), 1.46–1.22 (2H, m, $\overline{N}$CH₂CH₂); Found C, 71.09; $\overline{H}$, 6.84; N, 2.51. C₃₀H₃₅NO.C₂H₂O₄.0.3H₂O requires C, 71.19;H,6.86;N,2.67.m/e (EI) 425(M+), (CI+)426 (M+H), (CI−=)424 (M−H).

Chromatographic separation performed above (Example 1c) also yielded isomer B, which was recrystallized as an oxalate salt from ethanol/diethyl ether to give 3-[(3,5-dimethylphenyl)-1-azabicyclo[2.2.2]octane hydrogen oxalate salt isomer B; m.p. 128°–130° C.; C₃₀H₃₅NO.C₂H₂O₄.H₂O requires C, 72.03;H, 7.36;N,2.62. Found: C,71.96;H, 7.30;N, 2.62%.

The product of Example 1a was crystallized from diethyl ether. The mother liquor (enriched in one diastereomer) was reduced according to the procedure described (Example 1b) and alkylated (Example 1c) to give 3-[(3,5-dimethylphenyl) methyloxy)-2-(1,2-diphenylethyl)-1-azabicyclo[2.2.2]octane hydrogen oxalate isomer C m.p. 55°–58° C.; C₃₀H₃₅NO.1.5(C₂-

H₂O₄).H₂O requires C, 68.49;H,6.96; N, 2.42. Found: C,68.84; H,7.01;N, 2.60%.

The following Examples were prepared similarly.

EXAMPLE 2

3,5-bis-Trifluoromethylphenyl)methyloxy-2-(1,2-diphenylethyl)-1-azabicyclo[2.2.2]octane hydrogen oxalate salt The title compound was prepared from 2-(1,2-diphenylethyl)-3-hydroxy-1-azabicyclo[2.2.2]octane (Example 1b) using 3,5-bis-trifluoromethylbenzyl bromide to give:

Isomer A. m.p. 150°–153° C.; $C_{30}H_{29}NOF_6 \cdot C_2H_2O_4 \cdot 0.5H_2O$ requires C,60.75; H,5.09; N,2.21. Found: C,60.84; H, 4,85; N, 2.17%.

Isomer B m.p. 175°–177° C.; $C_{30}H_{29}NOF_6 \cdot C_2H_2O_4 \cdot 0.75H_2O$ requires C, 60.32; H, 5.14; N, 2.20. Found: C,60.44;H,5.11; N, 2.14%.

EXAMPLE 3

3-(3,5-bis-Trifluoromethylphenyl)methyloxy-2-[1-(1-(4-methoxyphenyl)-2-phenyl)ethyl]-1-azabicyclo[2.2.2]octane hydrogen oxalate salt Isomer A m.p. 83° C.; $C_{31}H_{31}NO_2F_6 \cdot 1.3(C_2H_2O_4)$ requires C,59.29;H,4.97;N, 2.05.Found:C,59.16;H,5.12;N, 2.12%.

EXAMPLE 4

3-(3,5-bis-Trifluoromethylphenyl)methyloxy-2-[1-(1-(3-methoxyphenyl)-2-phenyl)ethyl]-1-azabicyclo[2.2.2]octane hydrogen oxalate salt Isomer A m.p. 179°–180° C.; $C_{31}H_{31}NO_2F_6 \cdot C_2H_2O_4$ requires C, 60.64; H, 5.09; N, 2.14. Found: C, 60.28; H, 5.33; N, 2.16%.

Isomer B m.p. 148°–151° C.; $C_{31}H_{31}NO_2F_6 \cdot 3.6(C_2H_2O_4) \cdot 0.25CH_3COOCH_2CH_3$ requires C, 51.74; H, 4.35; N, 1.58. Found: C, 51.34; H, 4.77; N, 1.94%.

EXAMPLE 5

3-(3,5-Bis(trifluoromethyl)phenyl)methyloxy-2-(α-cyclohexylbenzyl)-1-azabicyclo[2.2.2]octane oxalate hemihydrate a) 2-(α-cyclohexylbenzyl)-3-oxo-1-azabicyclo[2.2.2]octane The title compound as a mixture of diastereomers was prepared in a manner analogous to that described in Example 1a using cyclohexylmagnesium chloride.

b) Using conditions analogous to those described in Example 1b and c the product of Example 5a was reduced and alkylated (with 3,5-bis(trifluoromethyl)benzyl bromide to give 3-(3,5-bis(trifluoromethyl) phenyl)-methyloxy-2-(α-cyclohexylbenzyl)-1-azabicyclo [2.2.2]octane oxalate hemihydrate, mp 119°–121° C. Found: C, 59.33; H, 5.67; N, 2.22. $C_{29}H_{33}NOF_6 \cdot C_2H_2O_4 \cdot 0.5(H_2O)$ requires C, 59.61; H, 2.24; N, 5.89%. m/e(CI³⁰)=526 (M+H), (CI⁻)=524 (M−H).

The following examples illustrate pharmaceutical compositions according to the invention.

EXAMPLE 6A

Tablets Containing 1–25 mg of Compound

| Amount mg | | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 6B

Tablets Containing 26–100 mg of Compound

| Amount mg | | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 7

Parenteral Injection

| Amount mg | |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 1 ml |

The sodium phosphate, citric acid monohydrate and sodium chloride are dissolved in a portion of the water. The compound of formula (I) is dissolved or suspended in the solution and made up to volume.

EXAMPLE 8

Topical Formulation

| Amount mg | |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1-receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 ug of the plasmid DNA into 10 million COS cells was achieved by electroporation in 800 μof transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM N-2-hydroxyethyl-piperazine-N'-2-ethane sulphonic acid (HEPES) pH 7.4) at 260 V and 950 μusing the IBI GENEZAPPER (trademark IBI, New Haven, Conn., USA). The cells were incubated in 10% fetal calf serum, 2 mM glutamine, 100 U/ml penicillin-streptomycin, and 90% DMEM media (GIBCO, Grand Island, N.Y., USA) in 5% $CO_2$ at 37° C. for three days before the binding assay.

B. Stable Expression in Chinese Hamster Ovarian Cell Line

To establish a stable cell line expressing cloned human NK1R, the cDNA was subcloned into the vector pRcCMV (INVITROGEN). Transfection of 20 ug of the plasmid DNA into CHO cells was achieved by electroporation in 800 μl of transfection buffer supplemented with 0.625 mg/ml Herring sperm DNA at 300 V and 950 μF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans., USA), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}I$-substance P ($^{125}I$-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to about 10,000 cpm of specific $^{125}I$-SP binding (approximately 50,000 to 200,000 cells). In the binding assay, 200 ul of cells were added to a tube containing 20 ul of 1.5 to 2.5 nM of $^{125}I$-SP and 20 μl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was prewetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The acitivation of phospholiphase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 5μCi of $^3H$-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3 nM to activate the human NK1R. After 30 min of incubation at 37° C., the medium is removed and 0.1 N HCl is added. Each well is sonicated at 4° C. and extracted with $CHCl_3$ methanol (1:1). The aqueous phase is applied to a 1 ml Dowex AG 1X8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The data in Table 1 were obtained for compounds of formula (I):

TABLE 1

| SUBSTANCE P ANTAGONISM RESULTS | |
|---|---|
| Compound of Ex # | $IC_{50}$ @ NK1R (nM) |
| 1: ISOMER A | 2.4 |
| 1: ISOMER B | 1.8 |
| 1: ISOMER C | >100 |
| 2: ISOMER A | 4.5 |
| 2: ISOMER B | 6.3 |
| 2: ISOMER C | >100 |
| 3: ISOMER A | 3.0 |
| 4: ISOMER A | 10.0 |
| 4: ISOMER B | 1.8 |
| 5 | 3.0 |

We claim:
1. A compound of formula (IC), or a salt or prodrug thereof:

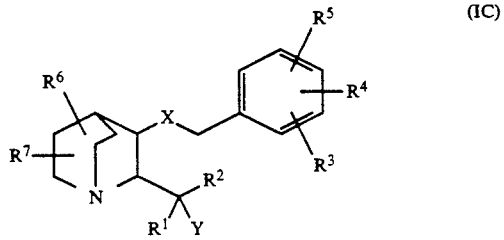

(IC)

wherein
X is selected from oxa and thia;
Y is selected from H and hydroxy;
$R^1$ is selected from phenyl, thienyl or $C_{5-7}$ cycloalkyl; wherein either phenyl or thienyl can be unsubstituted or substituted by a substituent selected from halo, trifluoromethyl or $C_{1-3}$ alkoxy;
$R^2$ is selected from benzyl or $C_{5-7}$ cycloalkyl, wherein benzyl can be substituted on the benzyl ring by a substituent selected from halo, trifluoromethyl or $C_{1-3}$ alkoxy; and
$R^3$, $R^4$ and $R^5$ are independently selected from H, $C_{1-6}$ alkyl, $C_{2-6}$ alkenyl, $C_{2-6}$ alkynyl, halo, cyano, nitro, trifluoromethyl, trimethylsilyl, —$OR^a$, $SCH_3$, $SOCH_3$, $SO_2CH_3$, —$NR^aR^b$, —$NR^aCOR^b$, —$NR^aCO_2R^b$, —$CO_2R^a$ and —$CONR^aR^b$; where $R^a$ and $R^b$ are independently selected from H, $C_{1-6}$ alkyl, phenyl and trifluoromethyl; and
$R^6$ and $R^7$ independently represent H, $C_{1-4}$ alkyl, $C_{2-4}$ alkynyl, halo, hydroxy, $C_{1-4}$ alkoxy, carboxy or ($C_{1-4}$ alkoxy) carbonyl; or $R_6$ and $R_7$ together represent carbonyl.

2. A compound according to claim 1, where Y is H; $R^3$, $R^4$ and $R^5$ are independently selected from H, $C_{1-6}$alkyl, $C_{2-6}$alkenyl, $C_{2-6}$alkynyl, halo, cyano, nitro, trifluoromethyl, —$OR^a$, —$NR^aR^b$, —$NR^aCOR^b$, —$NR^aCO_2R^b$, —$CO_2R^a$ and —$CONR^aR^b$, and $R^a$ and $R^b$ are independently selected from H and $C_{1-6}$alkyl.

3. A compound according to claim 1 wherein Q is a 1-azabicyclo[2.2.2]octanyl (quinuclidinyl) ring system and X is oxa.

4. A compound according to claim 1 wherein $R^1$ is selected from unsubstituted phenyl and phenyl substituted by methoxy and $R^2$ is selected from benzyl and cyclohexyl.

5. A compound according to claim 1 wherein $R^5$ is H and $R^3$ and $R^4$ are present at the meta-positions of the aromatic ring and are selected from methyl and trifluoromethyl.

6. A compound according to claim 1 selected from
3-[(3,5-dimethylphenyl)methyloxy]-2-(1,2-diphenylethyl)-1-azabicyclo[2.2.2]octane;
3-[(3,5-bistrifluoromethylphenyl)methyloxy]-2-(1,2-diphenylethyl)-1-azabicyclo[2.2.2]octane;
3-[(3,5-bistrifluoromethylphenyl)methyloxy]-2-[1-(1-(4-methoxyphenyl)-2-phenyl) ethyl]-1-azabicyclo[2.2.2]octane;
3-[(3,5-bistrifluoromethylphenyl)methyloxy]-2-[1-(1-(3-methoxyphenyl)-2-phenyl) ethyl]-1-azabicyclo[2.2.2]octane;
3-[(3,5-bistrifluoromethylphenyl)methyloxy]-2-(α-cyclohexylbenzyl)-1-azabicyclo [2.2.2]octane;
and salts and prodrugs thereof.

7. The compound of claim 1 wherein $R^6$ and $R^7$ are hydrogen.

8. A pharmaceutical composition comprising a compound according to claim 1 in association with a pharmaceutically acceptable carrier therefor.

9. A method for the treatment of a physiological disorder associated with an excess of tachykinins, which method comprises administration to a patient in need thereof of a tachykinin-reducing amount of a compound according to claim 1.

10. A method as claimed in claim 9 for the treatment of pain.

11. A method as claimed in claim 9 for the treatment of migraine.

* * * * *